US007892758B2

(12) United States Patent
Sharma et al.

(10) Patent No.: US 7,892,758 B2
(45) Date of Patent: Feb. 22, 2011

(54) USE OF N-MYRISTOYLTRANSFERASE ON NON-TUMOR TISSUE FOR CANCER DIAGNOSIS

(75) Inventors: Rajendra Kumar Sharma, Saskatoon (CA); Anuraag Shrivastav, Saskatoon (CA)

(73) Assignee: University of Saskatchewan, Saskatchewan (CA)

( * ) Notice: Subject to any disclaimer, the term of this patent is extended or adjusted under 35 U.S.C. 154(b) by 252 days.

(21) Appl. No.: 11/992,697

(22) PCT Filed: Sep. 26, 2006

(86) PCT No.: PCT/CA2006/001573

§ 371 (c)(1), (2), (4) Date: Mar. 27, 2008

(87) PCT Pub. No.: WO2007/036025

PCT Pub. Date: Apr. 5, 2007

(65) Prior Publication Data

US 2010/0068731 A1 Mar. 18, 2010

Related U.S. Application Data

(60) Provisional application No. 60/720,474, filed on Sep. 27, 2005.

(51) Int. Cl.
 *G01N 33/53* (2006.01)
(52) U.S. Cl. ....................................................... 435/7.1
(58) Field of Classification Search ........................ None
 See application file for complete search history.

(56) References Cited

FOREIGN PATENT DOCUMENTS

WO  WO 2004/016758  2/2004

OTHER PUBLICATIONS

Raju et al (Experimental Cell Research, 1997, 235: 145-154.*
Tockman et al (Cancer Res., 1992, 52:2711s-2718s).*
Greenbaum et al. (Genome Biology, 2003, vol. 4, Issue 9, pp. 117.1-117.8).*
Alberts et al. (Molecular Biology of the Cell, 3rd edition, 1994, p. 465).*
Rajala et al (Journal of Cellular Biochemistry, 2002, 86:509-519).*
Lu, et al., "Expression of N-myristoyltransferase in Human Brain Tumors", *Neurochemical Research*, vol. 30, No. 1, Jan. 2005, pp. 9-13.
Raju, et al., "N-Myristoyltransferase Overexpression In Human Colorectal Adenocarcinomas", *Experimental Cell Research*, 235, 145-154 (1997).
Magnuson et al. "Increased *N*-Myristoyltransferase Activity Observed in Rat and Human Colonic Tumors", *Journal of the National Cancer Institute*, 87:21 pp. 1630-1635 (1995).
Lu et al. "Expression of N-myristoyltransferase in Human Brain Tumors", *Neurochemical Research*, 30:1 pp. 9-13 (2005).
Selvakumar et al. "Myristoyl-CoA:protein N-myristoyltransferase: A novel molecular approach for cancer therapy (Review)", *International Journal of Molecular Medicine*, 10: pp. 493-500 (2002).
Cohen et al. "Cancer of the Colon", *Cancers of the Gastrointestinal Tract*, 32.7: pp. 1144-1197 (n.d.).
Graziano et al. "Prognostic molecular markers for planning adjuvant chemotherapy trials in Dukes' B colorectal cancer patients: how much evidence is enough?", *Annuals of Oncology*, 14: pp. 1026-1038 (2003).
Rajala et al. "N-myristoyltransferase", *Molecular and Cellular Biochemistry*, 204: pp. 135-155 (2000).
Shrivastav et al. "N-myristoyltransferase: A potential novel diagnostic marker for colon cancer", *Journal of Translational Medicine*, 5:58 (2007).
Raju et al. "*N*-Myristoyltransferase Overexpression in Human Colorectal Adenocarcinomas", *Experimental Cell Research*, 235: pp. 145-154 (1997).

* cited by examiner

*Primary Examiner*—Sean E Aeder
(74) *Attorney, Agent, or Firm*—Drinker Biddle & Reath LLP

(57) ABSTRACT

A diagnostic method and kit are disclosed for detection of cancer. Detection of elevated levels of N-myristoyltransferase (NMT) or NMT activity in blood or bone marrow, and specifically in peripheral blood mononuclear cells, can be used as a marker for cancer. The use of this method for detection of adenocarcinoma, such as colorectal cancer, is exemplified.

14 Claims, 6 Drawing Sheets

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial
<220> FEATURE:
<223> OTHER INFORMATION: N-terminal end of cAMP-dependent protein kinase

<400> SEQUENCE: 1

Gly Asn Ala Ala Ala Ala Lys Lys Arg Arg
1               5                   10
```

USE OF N-MYRISTOYLTRANSFERASE ON NON-TUMOR TISSUE FOR CANCER DIAGNOSIS

CROSS REFERENCE TO RELATED APPLICATIONS

This application claims priority from and derives the benefit of U.S. patent application 60/720,474 filed Sep. 27, 2005, the entirety of which is herein incorporated by reference.

FIELD OF THE INVENTION

The present invention relates generally to diagnostic methods for detection of cancer.

BACKGROUND OF THE INVENTION

Cancer is one of the leading causes of premature death worldwide. Furthermore, colorectal cancer is the second leading cause of death from cancer in the western world. Colorectal cancer is curable if diagnosed early. One of the major treatment protocols for colorectal cancer is surgery. With no additional therapy, surgery typically cures Duke's A colon cancer that invades the submucosa and Duke's B1 disease that invades the muscularis propria (Cohen et al., In: DeVita et al. (eds.), Cancer Principles and Practice of Oncology, Ed. 5, pp. 1144-1197. New York: Lippincott-Raven.).

The primary prognostic approach to identify differences among patients in early stages of the disease is the Tumor-Node-Metastasis (TNM) system (Graziano et al. (2003) Ann Oncol. 14, 1026-1038). However, the survival outcome varies among patients with similar pathological disease stages. There have been increasing demands to specify the molecular markers for more aggressive colorectal cancer in order to identify the disease well in advance and prescribe appropriate patient therapy. In response, new therapeutic strategies are needed to combat colorectal cancer.

It is known that the activity of N-myristoyltransferase (NMT) is highly elevated in colorectal cancer (Magnuson et al. 1995, J. Natl. Cancer Inst. 87, 1630-1635). NMT is an enzyme that catalyzes the myristoylation of proteins involved in diverse biological functions including oncogenesis (Rajala et al. (2000) Mol. Cell. Biochem. 204, 135-155; Selvakumar et al., (2002) Int. J. Mol. Med. 10, 493-500).

N-myristoyltransferase activity is increased in rat colonic tumors compared to those of normal appearing colonic mucosa (Magnuson et al., (1995) J. Natl. Cancer Inst. 87, 1630-1635.). Interestingly, NMT activity in the normal appearing mucosa of colon cancer bearing rats was similar to the activity found in colonic mucosa of control rats, suggesting that elevated NMT activity is restricted to the tumor site. Higher NMT activity is observed in rat colonic tumors when compared with the corresponding normal-appearing or normal mucosa. Furthermore, a several fold increase in NMT activity as compared to adjacent normal-appearing mucosa, was observed in polyps and stage B1 tumors located in the descending colon close to the rectum.

In addition to the rat model, elevated NMT activity and expression was also observed in human adenocarcinoma compared to that of normal appearing mucosa (Magnuson et al., (1995) J. Natl. Cancer Inst. 87, 1630-1635; Raju et al., (1997) Exp. Cell Res. 235, 145-154.). NMT activity in normal appearing mucosa is similar to that of Crohn's disease and the volvulus, indicating that elevated NMT activity is specific to cancer and is not a non-specific response to inflammatory conditions or noncancerous lesions. Rajala et al. (Cancer 2000; 88(9):1992-1999) showed increased expression on NMT in gall bladder tissue of patients with gall bladder cancer.

Previous work, however, has not established NMT as a marker for cancer, given the limitation that the elevated expression and activity of NMT in the tumor region is not accessible for prognostic/diagnostic purposes until a colonoscopy is performed and a tissue sample is available for protein analysis.

There is a need for non-invasive or minimally invasive technologies that can be used to detect cancer.

SUMMARY OF THE INVENTION

It is an object of the present invention to provide a method for detection of cancer.

In a first aspect, the present invention provides a method for the detection of cancer comprising the steps of obtaining a non-tumor tissue sample from a subject suspected of having cancer; and detecting an increased level of N-myristoyltransferase (NMT) or N-myristoyltransferase (NMT) activity relative to a control value.

In a further embodiment, there is provided a method for the detection of colorectal cancer comprising the steps of obtaining a blood sample from a subject suspected of having cancer; separating peripheral blood mononuclear cells from the blood sample, and detecting N-myristoyltransferase or N-myristoyltransferase activity in said peripheral blood mononuclear cells.

In further aspect, the present invention provides a kit for the detection of cancer, employing the inventive method. The kit comprises an anti-N-myristoyltransferase antibody and instructions for use. Additionally, a use of an anti-N-myristoyltransferase (NMT) antibody is disclosed, for detection of elevated NMT in a non-tumor tissue sample for diagnosis of cancer.

Additionally, an embodiment of the invention provides the use of an anti-N-myristoyltransferase (NMT) antibody for detection of elevated NMT in a non-tumor tissue sample for diagnosis of cancer. The kit may be of use in detection of epithelial cancers, for example, colorectal cancer. The non-tumor tissue sample may be, for example, peripheral blood mononuclear cells.

Further, a method is provided for the detection of colorectal cancer comprising the steps of obtaining a bone marrow sample from a subject suspected of having cancer; separating bone marrow cells from the sample, and detecting increased N-myristoyltransferase or N-myristoyltransferase activity in the bone marrow cells.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures.

DETAILED DESCRIPTION

Figure 1:
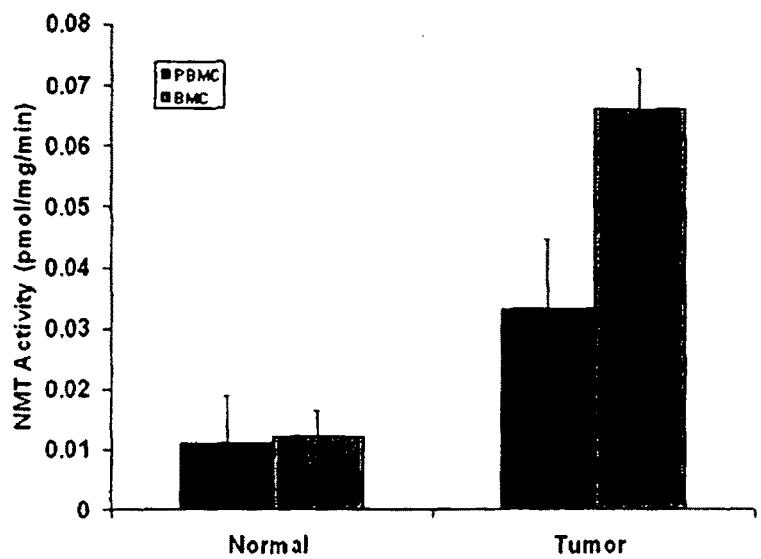
FIG. 1 illustrates NMT activity in peripheral blood mononuclear cells (PBMC) and Bone Marrow Cells (BMC) of normal and colon tumor bearing rats.

Generally, the present invention provides a method for the detection of cancer comprising the steps of obtaining a non-tumor tissue sample from a subject suspected of having cancer; and detecting an increased level of N-myristoyltransferase (NMT) or N-myristoyltransferase (NMT) activity relative to a control value.

Previously, it was believed that only tumor tissue contained elevated levels or activity of NMT. However, according to the invention, non-tumor tissues may be obtained and increased NMT or NMT activity is also indicative of cancer. Exemplary non-tumor tissues include, but are not limited to blood or bone marrow. Using blood samples for the detection of NMT or NMT activity provides the extra advantage that it is minimally invasive to withdraw a blood sample from a patient. Thus, no surgical or invasive procedure is required to remove tumorous tissue. The blood sample can be drawn, for example, in a physician's office during an annual physical check-up, which would allow the method to be conducted routinely on a large number of subjects. Early screening and detection will greatly increase the likelihood of a positive outcome in the cases where cancer is detected.

When the non-tumor tissue sample is blood, it is especially advantageous to isolate or separate peripheral blood mononuclear cells, and assess NMT or NMT activity in these cell types.

A variety of methodologies or laboratory assays may be conducted to detect NMT or NMT activity. For example, immunohistochemical analysis may be used, wherein the level of NMT is detected by quantifying binding between NMT with an anti-NMT antibody. A polyclonal or monoclonal antibody may be used, for example, the anti-NMT polyclonal antibody as described by Raju et al. (1996) Protein Expr. Purif. 7:431-437. As would be clear to a person of skill in the art, an epitope or portion of a polyclonal antibody that is capable of binding with NMT may be cloned into a monoclonal antibody for use with the invention, using standard laboratory techniques.

Any cancer that leads to an increase in NMT level or activity in non-tumor tissue may be detected using the method of the invention. Exemplary cancers include adenocarcinomas, and epithelial cancers. Among these exemplary cancers, the method is advantageously used to detect colorectal cancers. As referred to herein, the term "colorectal cancer" is used to describe a cancer of the colon or rectum, which may or may not be an adenocarcinoma. An example of a colorectal cancer is colon cancer.

In the case where NMT activity is detected and assessed relative to a control value, a protein myristolation reaction with myristoyl-CoA can be used to detect activity. It is advantageous to assess this activity in peripheral blood mononuclear cells isolated from a blood sample. Thus, according to an embodiment of the invention, there is provided a method for the detection of colon cancer comprising the steps of obtaining a blood sample from a subject suspected of having cancer; separating peripheral blood mononuclear cells from the blood sample, and detecting N-myristoyltransferase or N-myristoyltransferase activity in the peripheral blood mononuclear cells.

A control value can be obtained in order to assess NMT or NMT activity against a range of standard or "normal" values, so that abnormal values can be detected. A subject's own previous values can be used as a "control" value, for those individuals who are monitored for cancer development on an ongoing basis. For example, those individuals suspected of having a familial susceptibility to cancer may be initially screened through a variety of means, including NMT levels and/or NMT activity levels, and should negative tests result, the NMT levels and/or NMT activity levels obtained can be used as a control for the individual against which to evaluate future measurements. In this way, the control value may be personalized. Alternatively, the NMT level or NMT activity level can be evaluated against a range of levels found in a non-cancerous control population. In this instance, the range of values provided can be used to define a confidence interval appropriately selected by the physician or clinical evaluator assessing the test. In the instance where immunohistochemical means are used to evaluate a sample against a control, the confidence interval may be selected, for example at a value from 80% to 95%, which may depend upon such parameters as the number of observations considered to arrive at the control value, and variability within and among subjects.

The method of the invention may be conducted using a kit containing selected reagents required to conduct the method in a typical clinical laboratory setting. For example, the kit may include an anti-N-myristoyltransferase antibody for detection of NMT, along with instructions for use of the kit. In this way, the test could be conducted on a blood sample sent to any clinical laboratory once the kit is obtained. The kit is particularly advantageous in detection of colon cancer, using peripheral blood mononuclear cells isolated from a subject's blood sample. This use of an anti-N-myristoyltransferase (NMT) antibody for detection of elevated NMT in a non-tumor tissue sample is advantageously an expedient and minimally invasive method for detection and diagnosis of cancer.

Previously, NMT was not considered for use in detection of cancer due to the limitation that the elevated expression and activity of NMT in the tumor region is not accessible for prognostic/diagnostic purposes until after colonoscopy is performed and a tissue sample is available for analysis. However, the invention is based, in part, on the surprising discovery that detection of NMT in blood samples derived from tumor bearing animal subjects and human cancer patients is indicative and predictive of cancer. Thus, the in vitro kit according to the invention can be used for detection of NMT as a diagnostic tool for cancer detection.

The following characteristics may be observed in tumor bearing subjects: the presence of NMT activity in the blood; elevation of NMT activity and expression in peripheral blood mononuclear cells (PBMC); and elevation of NMT activity and expression in bone marrow (BM).

Anti-NMT antibodies, such as monoclonal or polyclonal anti-NMT antibodies can be used for immunohistochemical analysis. Immunohistochemical evidence for positive staining of NMT in the blood and BM of tumor bearing hosts may be used to detect the presence of tumors.

A simple prognostic/diagnostic tool for cancer, and in particular: colorectal cancer, is provided which does not require surgery or biopsy. Moreover, this marker for colorectal cancer in peripheral blood is not associated with an inflammatory response due to the growth of the tumor as is the case for other markers of colorectal cancer, for example, as reported by Erlinger of al. (2004) JAMA. 291, 585-590.

EXAMPLE 1

NMT Detection as a Marker of Colorectal Cancer

In this example, NMT is detected in peripheral blood and bone marrow, and is shown to be a predictive marker of the presence of tumors.

Material and Methods. [9, 10-$^3$H Myristic acid (39.3 Ci/mMol)] was purchased from Perkin Elmer (Boston, USA). Pseudomonas acyl CoA synthetase, phenylmethylsulfonyl fluoride (PMSF), dithiothretol (DTT), soybean trypsin inhibitor, pepsin and benzamidine were from Sigma Chemical Co. (Toronto, Canada). Peptide substrate derived from the N-terminal ends of cAMP-dependent protein kinase A (GNAAAAKKRR) (SEQ ID NO:1) was synthesized by the Alberta Peptide Institute, Canada, and this sequence was published previously by King and Sharma (Anal Biochem, 1991; 199:149-153). Monoclonal anti-NMT antibody was purchased from BD Biosciences (Mississauga, Canada). Polyclonal anti-NMT antibody was raised in the laboratory. Recombinant hNMT was purified as described by Raju et al. (1996) Protein Expr. Purif 7, 431-437. PVDF membrane was procured from BioRad Laboratories (Herculus, USA). Chemiluminescence agents were from Perkin Elmer Life Sciences. HRP-conjugated secondary and anti-von Willebrand antibodies for immunohistochemistry were purchased from Dako Corporation (Carpenteria, USA). General laboratory reagents were obtained from Sigma Chemical Co. and were of analytical grade.

Azoxymethane-Induced Colonic Tumors in Rats. Twenty Sprague-Dawley rats (weighing, Males: 250.8±15.5; Female: 168.1±9.02) were obtained from Charles River Canada (St. Constant, Canada). Rats were acclimatized for one week and randomly allocated to treatment or control groups. Twelve rats (six male and six female) were given eight weekly subcutaneous injections of azoxymethane (10 mg/kg of body weight) in saline. Eight control rats (four male and four female) were given eight weekly injections of saline only. Animals were given rat chow and water ad libitum and housed two per cage. Temperature, humidity and light were controlled at 22° C., 50% and 12/12hours (light/dark) respectively. All animals were cared for in accordance with the guidelines of the Canadian Council of Animal Care Subcommittee of the National Research Council. Animals were killed after 30 weeks by $CO_2$ asphyxiation. Peripheral blood was drawn from tail and blood smears were made on a glass slide for immunohistochemical studies. Blood from main artery was collected in a Vacutainers™ containing EDTA for the separation of mononuclear cells. The colons were removed followed by flushing of ice-cold saline to remove contents. Further colons were slit longitudinally, and opened flat on an ice cold surface to count for size and number of tumors.

Separation of Peripheral Blood Mononuclear Cells. Peripheral blood samples were used immediately for the separation of mononuclear cells. One milliliter of blood was diluted with an equal volume of RPMI medium (without serum). Diluted peripheral blood was layered onto 8 mL of Ficoll-Paque™ (Amersham Biosciences, USA) in 15 mL conical tubes and centrifuged at 800×g (Beckman, TJ-6 model, USA). Cells were then gently removed from the plasma/ficoll interface without disturbing the layers. Cells were transferred to a 15 mL conical tube and washed with an equal volume of PBS. The isolated peripheral blood mononuclear cells (PBMC) were then resuspended in RPMI medium and cell counts and viability determined. Further, PBMC were lysed in RIPA buffer containing 1 mM PMSF, 10 mM DTT and 1% protease inhibitor cocktail (Sigma, Canada).

Isolation of Bone Marrow. Bone marrow (BM) was obtained by flushing PBS into the femurs of rats by 22 gauge needle and syringe. Bone marrow was homogenized in RIPA buffer as above. For immunohistochemical studies, BM was fixed in formaldehyde and, following dehydration in ascending concentrations of ethanol and xylene, was embedded in paraffin. Bone marrow cells (BMC) were also obtained from the femurs of rats. BMC were agitated gently to prepare a single cell suspension and were washed subsequently thrice in PBS. BMC were then incubated for 24 h in humidified air and 5% $CO_2$ at 37° C. After washing, the cells remaining adhered to the plastic culture plates were bone marrow macrophages. Cells were lysed in RIPA buffer as above and were subjected to Western analysis and NMT assay. Single cell suspensions of BMC were made from bone marrow and were cultured in RPMI medium for 24 h and were lysed in RIPA buffer for NMT expression and activity. Total bone marrow was embedded in paraffin for immunohistochemical analysis.

N-Myristoyltransferase Assay. N-Myristoyltransferase activity was assayed as described by King and Sharma (1991) Anal Biochem. 199, 149-153. Briefly, [$^3$H]myristoyl-CoA was synthesized as described earlier (Raju et al., (1999) Methods Mol. Biol. 116, 193-211). The reaction mixture contained 40 mM Tris-HCl, pH 7.4, 0.1 mM EGTA, 10 mM $MgCl_2$, 5 mM ATP, 1 mM LiCoA, 1 μM [$^3$H]myristic acid (7.5 μCi) and 0.3 unit/mL Pseudomonas acyl-CoA synthetase in a total volume of 200 μL. The reaction was carried out for 30 min at 30° C. The conversion to [$^3$H]myristoyl-CoA was generally greater than 95%. The assay mixture contained 40 mM Tris-HCl, pH 7.4, 0.5 mM EGTA, 0.45 mM 2-mercaptoethanol, 1% Triton X-100, peptide substrate (500 μM) and NMT in a total volume of 25 μL. The transferase reaction was initiated by the addition of freshly generated [$^3$H]myristoyl-CoA and was incubated at 30° C. for 30 minutes. The reaction was terminated by spotting 15 μL aliquots of incubation mixture onto P81 phosphocellulose paper discs and drying under a stream of warm air. The P81 phosphocellulose paper discs were washed in two changes of 40 mM Tris-HCl, pH 7.3 for 60 minutes. The radioactivity was quantified in 7.5 mL of Beckman Ready Safe™ Liquid Scintillation mixture in a Beckman Liquid Scintillation Counter. One unit of NMT activity was expressed as 1 pmol of myristoyl peptide formed per min.

Western Blot Analysis. Western blot analysis was performed essentially as described by Towbin et at (1979) Proc Natl Acad Sci USA. 76, 4350-4354. Samples were electrophoresed on a SDS-PAGE and transferred to PVDF membrane. Transblotted PVDF membrane was incubated with blocking buffer (PBS-Tween™ 20 plus 5% powdered milk) for 1 h at room temperature to block non-specific binding.

After washing, the blot was incubated at 4° C. overnight with monoclonal antibody against NMT-1 (1:250, dilution in blocking buffer). After washing, the blot was incubated with HRP-conjugated goat anti-mouse secondary:antibody (1:5000, dilution in blocking buffer) and the NMT band was detected using the chemiluminescence reagent plus and exposed to X-ray films.

Immunohistochemistry. Labeled streptavidin avidin technique (Warnke et al., (1980) J. Histochem Cytochem. 28, 771-776) was used to localize the primary antibodies after microwave antigen retrieval. The primary antibodies used in this study were: CD3 (polyclonal, 1:80 dilution, Neomarkers, Fairmont, Calif.), CD20 (monoclonal, 1:20 dilution, Dako, Mississauga, ON), and NMT (polyclonal, 1:50 dilution). Immunohistochemical staining results were evaluated in a semi-quantitative manner as follows: number of mononuclear cells positive: none; rare; 10%; 10-30%, 30-50%, >50%. Staining intensity was evaluated as being absent, weak, moderate or strong.

Other Methods. Proteins were estimated by Bradford method (Bradford (1976) Anal Biochem. 72, 248-254). GraphPad Prism® software was used to calculate 95% confidence intervals.

Results and Discussion

In thirty weeks, all the animals' injected with azoxymethane developed at least two tumors in colon with a maximum of four in two cases. Control rats appeared healthy without any colon tumors. The histologic evaluation of these tumors showed that they ranged from adenoma (polyp) to highly invasive C2 tumors, based on the modified Duke's staging system (Astler et al. (1954) Ann Surg. 139, 846-852).

N-Myrsitoyltransferase Activity In Peripheral Blood Mononuclear Cells and Bone Marrow. N-Myristoyltransferase activity was measured in the PBMC and BMC of control (n=8) and tumor bearing rats (n=12). NMT activity was significantly higher in PBMC and BMC of tumor bearing rats compared to control rats (P=0.001).

FIG. 1 shows NMT activity in peripheral blood mononuclear cells (PBMC) and bone marrow cells (BMC) of normal and colon tumor bearing rats. Isolated peripheral blood mononuclear cells from peripheral blood of control or tumor bearing rat were assessed for NMT activity as described in "Materials and Methods". NMT activity was assayed using cAMP-dependent protein kinase derived peptide substrate. Values are mean±SD of three independent experiments.

FIG. 1 illustrates that NMT activity was approximately three fold higher in PBMC of tumor bearing rats, versus control animals. Interestingly, the highest NMT activity (almost ten fold) comparatively was observed in the PBMC of two tumor bearing rats with highly invasive C2 tumors. Whereas, approximately six folds higher NMT activity was observed in the BMC of the colon tumor bearing rats. The elevated NMT activity is reported for the first time in the blood sample. This increased NMT activity in the PBMC may serve as a diagnostic tool for colon cancer.

N-Myrsitoyltransferase Expression in Peripheral Blood Mononuclear Cells and Bone Marrow. Western blot analysis was performed to investigate whether higher activity of NMT in PBMC and BMC of tumor bearing rats is due to the absolute increase in the production of NMT or to the removal of the inhibitor or appearance of the activator of NMT. The expression of NMT in PBMC and BMC was three fold higher in tumor bearing rats compared to control rats. The NMT activity is directly proportional to protein expression in PBMC and BMC of tumor bearing rats.

Figure 2:
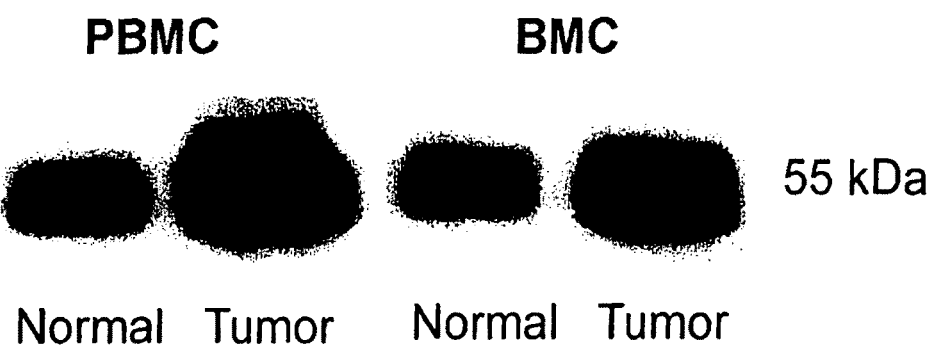
FIG. 2 shows the results of Western blot analysis of peripheral blood mononuclear cells and bone marrow cells.

FIG. 2 shows the Western blot analysis of peripheral blood mononuclear cells and bone marrow cells of normal and colorectal tumor bearing rats. Proteins (25 µg) from PBMC or BMC of control or tumor bearing rats were subjected to 10% SDS-PAGE, transblotted onto nitrocellulose membrane and were probed with monoclonal anti-human NMT antibody (1:250 dilution) as described under "Materials and Methods".

FIG. 2 shows that there is overexpression of NMT in the PBMC and BMC of tumor bearing rats as a consequence of the development of the tumor.

Immunohistochemistry. Once it was established that there is elevated activity and overexpression of NMT in the PBMC of tumor bearing host the incidence of colon cancer through routine diagnostic technique was then determined. NMT activity and Western blot analysis involve lengthy processes of separating mononuclear cells which are then lysed to obtain protein sample for analysis. Hence the potential of NMT as a diagnostic tool for colon cancer by immunohistochemical studies of blood was evaluated. Both monoclonal anti-NMT and polyclonal anti-NMT antibodies for immunohistochemical studies were used. An anti-NMT polyclonal antibody showed immunohistochemical staining and was used for immunohistochemical analysis. Blood smears were stained and probed with anti-CD3, anti-CD20 and anti-NMT antibodies for immunohistochemical studies. In peripheral blood, the majority of the mononuclear cells were CD3+ T-cells (75-80%) admixed with a smaller number of CD20+ (10-15%) B-cells (Data not shown) were observed.

Figure 3:
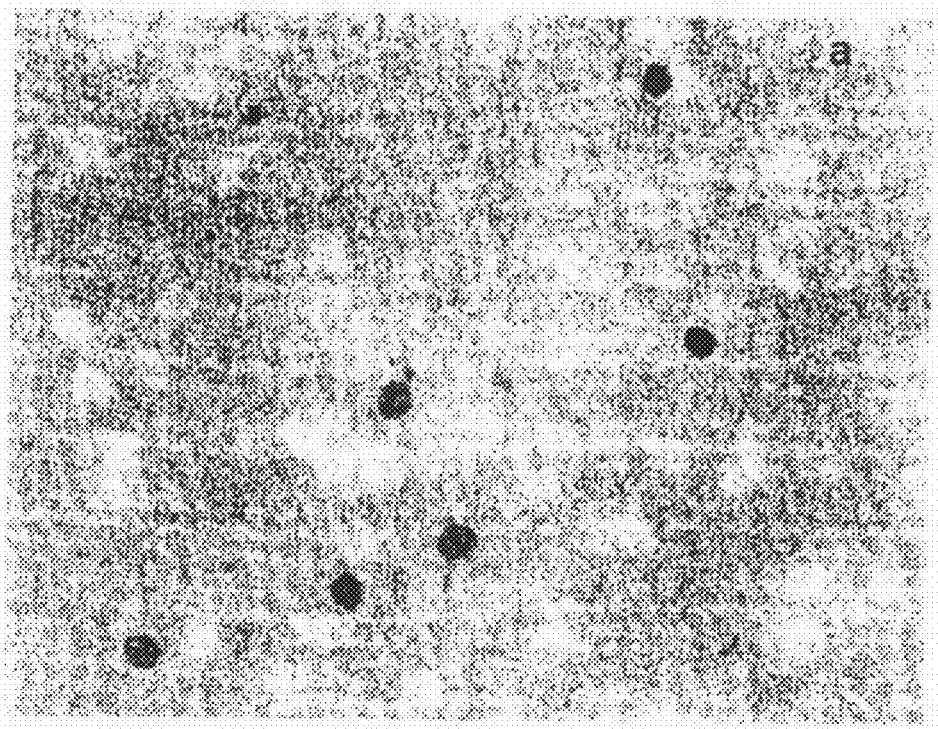
FIG. 3 illustrates immunohistochemical analysis of peripheral blood cells from control rats, devoid of NMT staining.
Figure 4:
FIG. 4 illustrates immunohistochemical analysis of peripheral blood mononuclear cells of tumor bearing rats, showing strong staining as evidence of intense NMT expression.

FIG. 3 and FIG. 4 illustrate the results of immunohistochemical analysis of peripheral blood cell smears of peripheral blood mononuclear cells (PBMC) incubated with anti-NMT antibody as described in "Materials and Methods". FIG. 3 shows that peripheral blood mononuclear cells (primarily lymphocytes) from control rats were devoid of NMT staining. FIG. 4 shows intense NMT expression observed in the peripheral blood mononuclear cells of colorectal tumor bearing rats as evident from strong staining (see arrows). In cases with tumors, NMT expression was moderate-strong in more than 50% of mononuclear cells (FIG. 4) while it was absent in controls (FIG. 3).

NMT overexpression was observed in cases of mononuclear cells of rats with highly invasive C2 tumors. NMT positively was also detected in the peripheral blood neutrophils. NMT expression was not observed in monocytes. The strikingly distinct NMT expression results obtained from the animal model are useful in establishing a simple diagnostic tool in human blood samples of colorectal cancer patients. We further studied expression of NMT in bone marrow of normal and colonic tumor rats.

Figure 5:
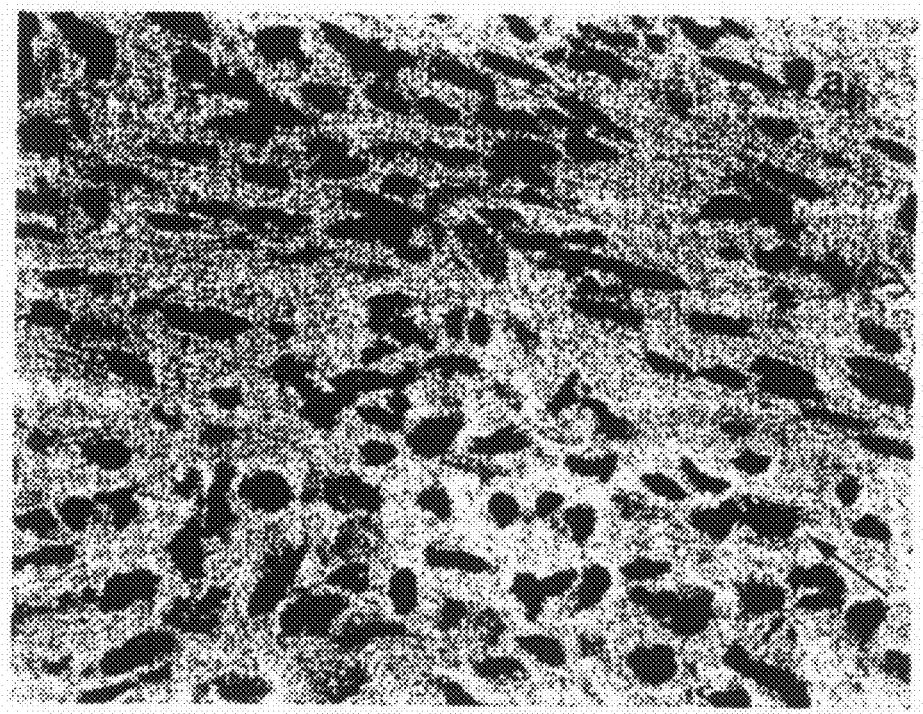
FIG. 5 shows immunohistochemical analysis of NMT staining in normal rat bone marrow.
Figure 6:
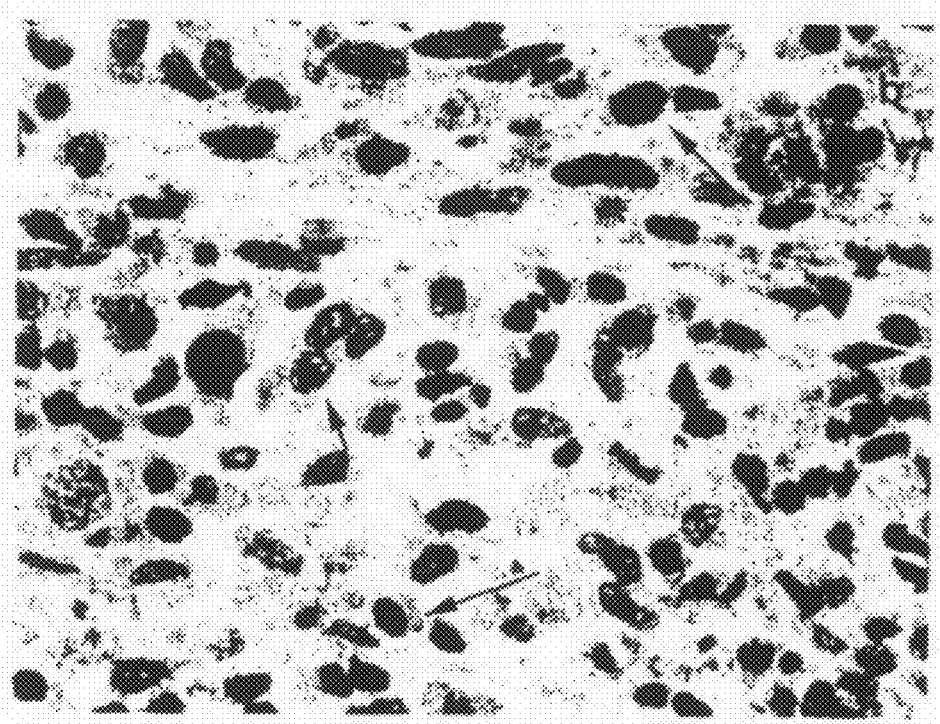
FIG. 6 shows immunohistochemical analysis of NMT staining in colonic tumor rat bone marrow.

FIG. 5 and FIG. 6 illustrate immunohistochemical analysis of bone marrow slides prepared from paraffin embedded blocks of bone marrow from normal and colonic tumor-bearing rats, respectively. Immunohistochemical analysis was carried out as described under "Materials and Methods".

FIG. 5 shows that cytoplasmic NMT staining in normal bone marrow cells (see arrow) was weak to faint. FIG. 6 shows that NMT was intensely stained in bone marrow of tumor bearing rats. In addition to its overexpression, a further interesting observation is that the immunohistochemical analysis of bone marrow of tumor bearing animal showed nuclear staining of NMT (see arrows indicating areas of nuclear localization of NMT). The presence of NMT in nucleus of bone marrow in case of colon cancer can serve as a diagnostic/prognostic marker.

Preliminary studies indicated that higher expression was also observed in human patients.

Without wishing to be limited to theory, it is possible that the elevated NMT activity in PBMC during colonic carcinogenesis may be due to the higher demand of myristoylation in various proteins/oncoproteins which are overexpressed and activated during tumorigenesis. For instance, the levels of the myristoylated tyrosine kinases, pp 60c-src and pp 60c-yes are several folds higher in colonic preneoplastic lesions and neoplasms compared with normal colon cells (Bolen et al., (1987) Proc. Natl. Acad. Sci. USA. 84, 2251-2255; Termuhlen at al., (1993) J. Surg. Res. 54, 293-298; Weber at al., (1992) J. Clin. Invest. 90, 815-821). One of the possible outcomes of the high NMT activity in neoplasia may be the aberrant myristoylation of proteins which are otherwise not usually myristoylated. For example, N-myristoylation of the normal cellular p21 ras resulted in potent transformation activity (Buss et al., (1989) Biochem. Soc. Trans. 17, 867-869). The myristoylation of H-ras and K-ras altered the subcellular localization and significantly affected the activation of MAP kinase (Cadwallader et al., (1994) Mol. Cell. Biol. 14, 4722-4730).

EXAMPLE 2

N-Myristoyltransferase as a Diagnostic Marker for Colorectal Cancer in Humans Colorectal cancer is the second leading cause of cancer deaths in the western world. If detected early, colorectal cancer is one of the most treatable forms of cancer. Unfortunately, very few people are screened. N-myristoyltransferase (NMT) catalyzes myristoylation of various proteins including oncoproteins. The data provided in this example demonstrate alteration of NMT activity during the progression of colorectal cancer in humans and establish NMT as a diagnostic marker for cancer.

The experimental design used in this example involves peripheral blood samples and bone marrow collected from human colon cancer patients and their controls. NMT activity and expression was determined as reported in Example 1. Immunohistochemical studies were carried out using standard procedures.

The results presented in this example demonstrate altered expression and localization of NMT in the peripheral blood and bone marrow in colon cancer patients. Immunohistochemical analysis revealed weak to negative staining for NMT in peripheral blood mononuclear cells (PBMC) of controls, whereas strong positively was observed in PBMC colon cancer patients. NMT was localized mostly in the nuclei of the bone marrow (BM) mononuclear cells of the colon cancer patients, whereas NMT remained cytoplasmic in the control bone marrow specimens.

The strikingly different NMT expression demonstrates the use of this marker as an investigative tool for screening or diagnosis of patients at risk for or suspected of having colon cancer.

Materials and Methods

The sources of chemicals and biochemicals are as described earlier (Shrivastav et al., Cancer Res 2003;63 (22): 7975-8). Peptide substrate derived from the N-terminal ends of cAMP-dependent protein kinase A (GNAAAAKKRR) (SEQ ID NO:1) was synthesized by the Alberta Peptide Institute, Canada. Monoclonal antibodies were purchased from BD Biosciences (Mississauga, Canada). Polyclonal antibodies were raised against purified human NMT in New Zealand white rabbits and the specificity of this antibody has been described previously by Raju et al., Exp Cell Res 1997;235 (1):145-54.

Blood sample collection. Peripheral blood samples were collected from the colon cancer patients (n=8) and controls (n=5) following informed consent according to the guidelines of University of Saskatchewan. Blood smears were prepared for immunohistochemical studies.

Separation of Peripheral Blood Mononuclear Cells (PBMC). Peripheral blood samples were used immediately for the separation of mononuclear cells. PBMC were isolated using Ficoll-Paque™ according to standard procedures. The isolated PBMC were then resuspended in RPMI medium and cell counts and viability determined. Further, PBMC were lysed in RIPA buffer containing 1 mM PMSF, 10 mM DTT and 1% of protease inhibitor cocktail.

Immunohistochemistry. Five µm thick sections of bone marrow were prepared from archival blocks and placed on glass slides. Bone marrow sections were used from three patients with colon cancer and three controls with no history of any kind of cancer. Labelled streptavidin-avidin technique was used to localize the primary antibodies after microwave antigen retrieval. The primary antibodies used in this study were: anti-CD3 (polyclonal, 1:80 dilution, Neomarkers, Fairmont, Calif.), anti-CD20 (monoclonal, 1:20 dilution, Dako, Mississauga, ON), and anti-NMT (polyclonal, 1:50 dilution). Immunohistochemical staining results were evaluated in a semi-quantitative manner as follows: number of mononuclear cells positive: none; rare-10%; 10-30%, 30-50%, >50%. Staining intensity was evaluated as being absent, weak, moderate or strong.

N-Myristoyltransferase Assay. [$^3$H]myristoyl-CoA was synthesized and N-Myristoyltransferase activity was assayed as described previously (Shrivastav et al., Cancer Res 2003; 63 (22):7975-8). The assay mixture contained 40 mM Tris-HCl, pH7.4, 0.5 mM EGTA, 0.45 mM 2-mercaptoethanol, 1% Triton X-100, peptide substrate (500 µM) and NMT in a total volume of 25 µL. The transferase reaction was initiated by the addition of freshly generated [$^3$H]myristoyl-CoA and was incubated at 30° C. for 30 min. One unit of NMT activity was expressed as 1 pmol of myristoyl peptide formed per min.

Western Blot Analysis. SDS-PAGE was carried using standard procedures and Western blot analysis was performed as described previously by Shrivastav et al., Cancer Res 2003; 63 (22):7975-8, and probed with monoclonal antibody against NMT-1 (1:250, dilution in blocking buffer).

Proteins were estimated by Bradford method using BSA as standard.

Results

Peripheral blood smears from colon cancer patients and healthy controls were stained and probed against anti-CD3, anti-CD68, anti-CD20 and anti-NMT antibodies. In peripheral blood, the majority of the mononuclear cells were CD3 positive T-cells (75-80%) admixed with a smaller number of CD20 positive (<5%) B-cells. CD68 positively was present in about 15% of cells, mostly monocytes.

Figure 7:
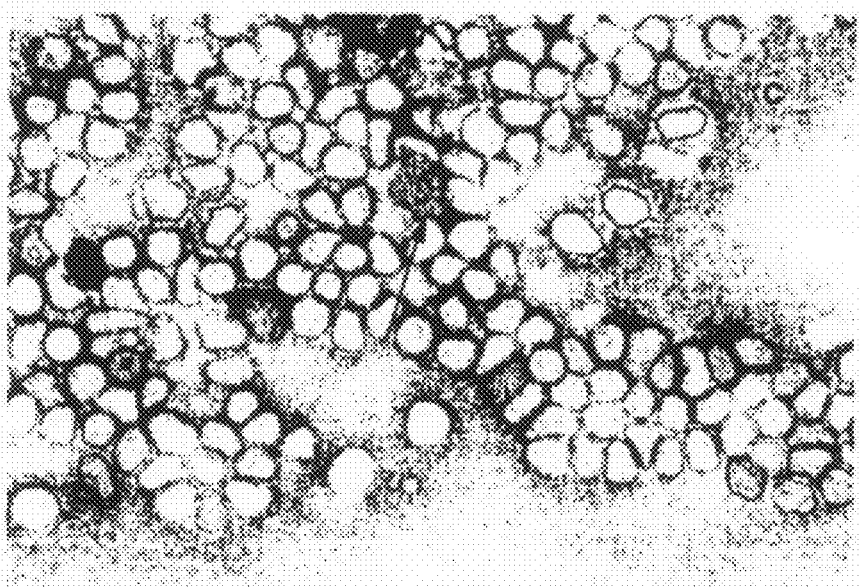
FIG. 7 shows negative NMT staining of lymphocytes.
Figure 8:
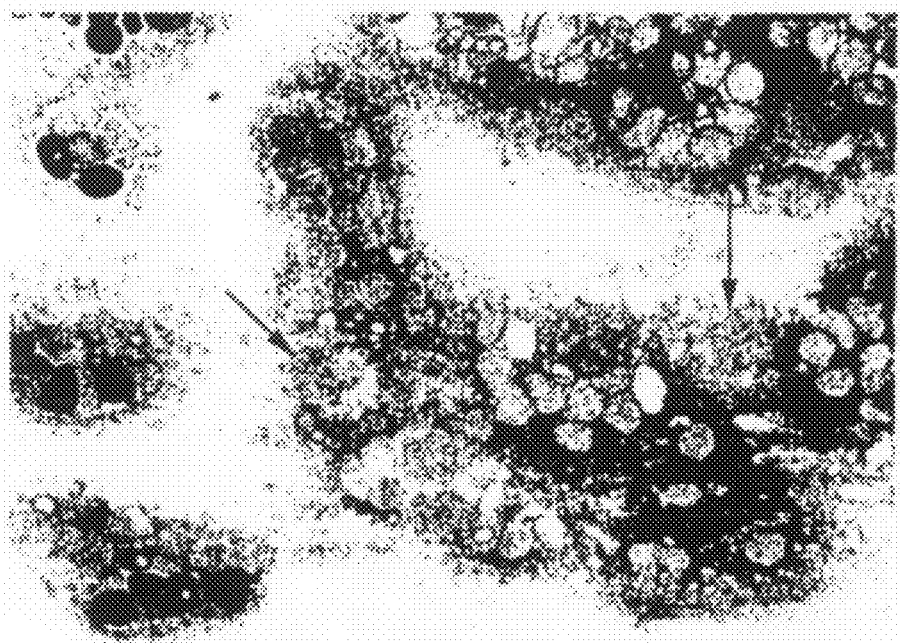
FIG. 8 shows negative NMT staining in monocytes of peripheral blood smear in control subjects.

FIG. 7 and FIG. 8 show NMT staining in the mononuclear cells (including lymphocytes and monocytes) and neutrophils in the peripheral blood smears of the healthy controls ranged from negative to rare weak positively. Strong NMT staining was observed in lymphocytes (see arrow in FIG. 7), monocytes (see arrows in FIG. 8), and neutrophils in the blood smear of the colon cancer patient.

Figure 9:
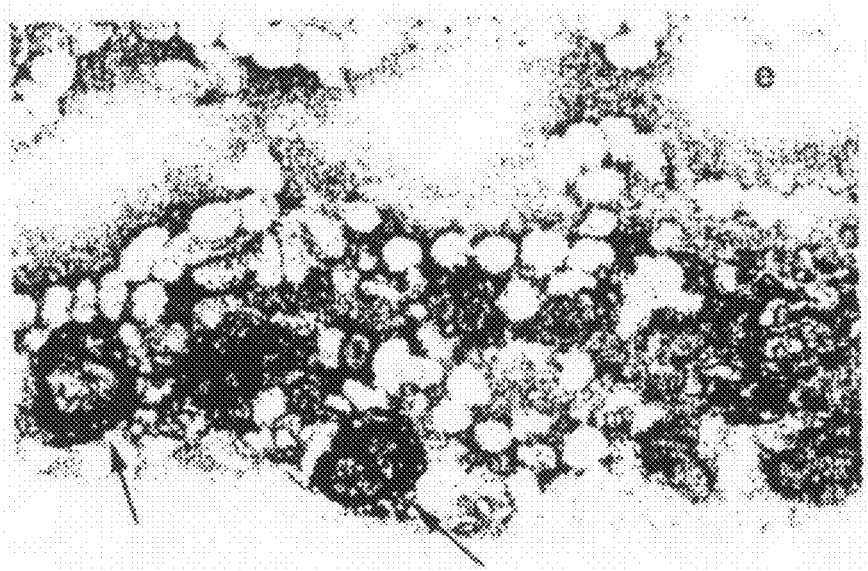
FIG. 9 shows a peripheral blood smear of a colon cancer patient, illustrating positive staining of macrophages.

FIG. 9 shows a peripheral blood smear of a colon cancer patient, illustrating positive staining of macrophages.

Figure 10:
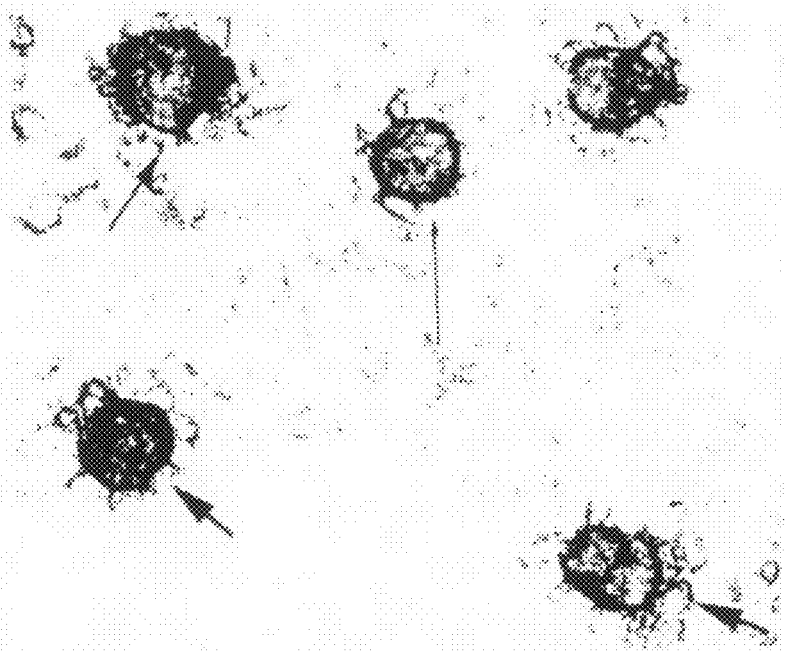
FIG. 10 is a peripheral blood smear of a colon cancer patient, illustrating positive staining of neutrophils, lymphocytes and macrophages.

FIG. 10 is a peripheral blood smear of a colon cancer patient, illustrating positive staining of neutrophils, lymphocytes and macrophages.

Figure 11:
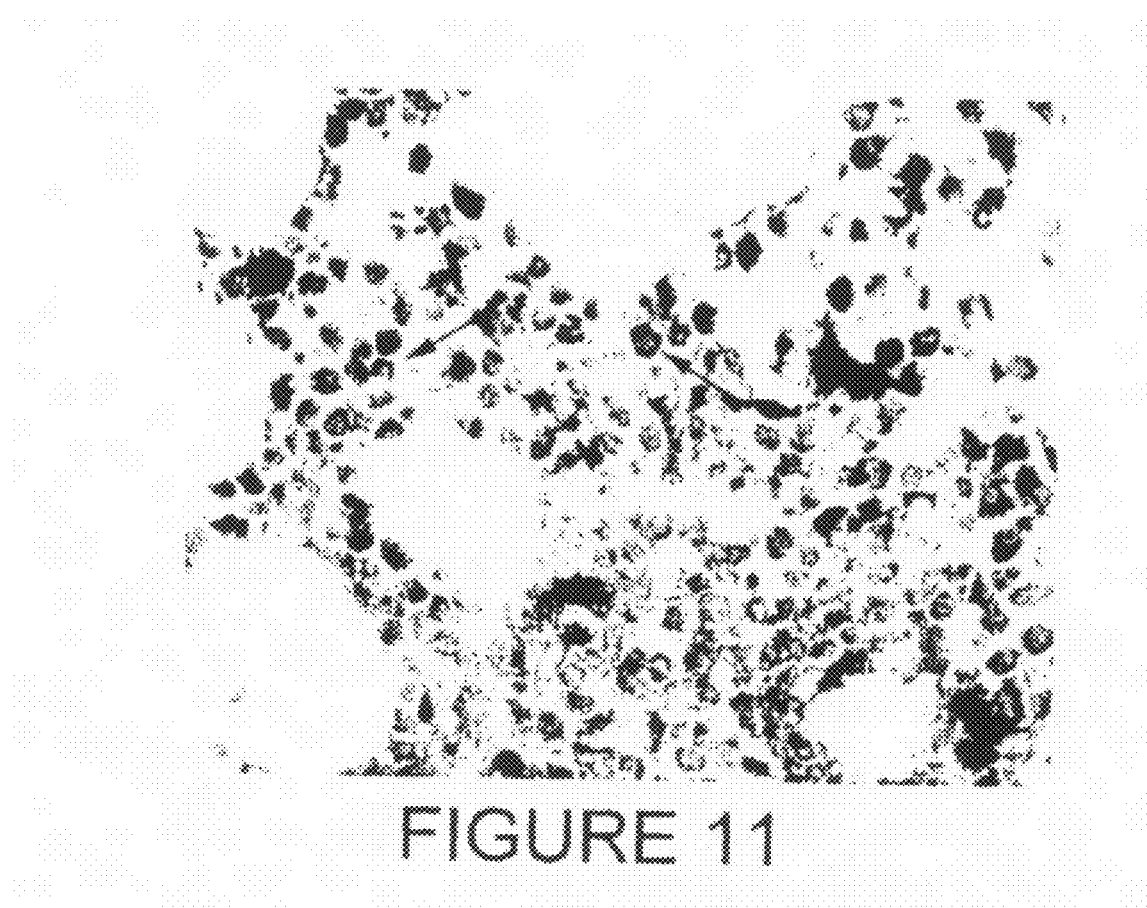
FIG. 11 shows NMT staining in bone marrow of control subjects.
Figure 12:
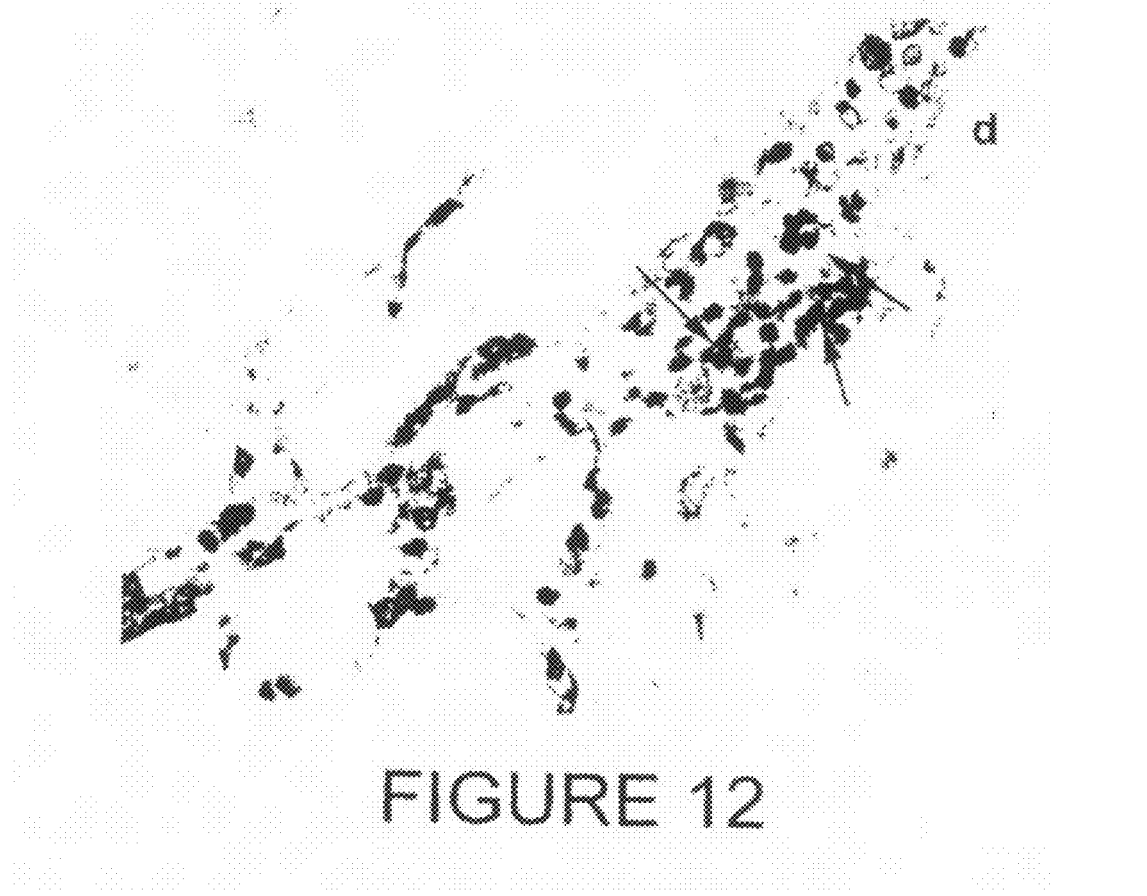
FIG. 12 shows intense nuclear and some cytoplasmic staining for NMT in bone marrow of a colon cancer patient.

FIG. 11 and FIG. 12 illustrate immunohistochemical analysis of bone marrow sections of control subjects and colon cancer patients, respectively. In FIG. 12, NMT was found to be localized in the nuclei as well as in the cytoplasm of the bone marrow mononuclear cells of the colon cancer patients, whereas NMT remained cytoplasmic in the control bone marrow specimens, as shown in FIG. 11.

The strikingly different NMT expression illustrates the ability of this marker to serve as an investigative tool for screening and/or diagnosis of patients at risk for or suspected of having colon cancer. Furthermore, altered localization of NMT in BM of tumor bearing hosts can serve as an added investigative tool for diagnostic purposes.

To assess the specificity of the test, immunohistochemical staining of the peripheral blood from a chronic lymphocytic leukemic (CLL) patient was undertaken. NMT staining was negative in the lymphoid cells of the CLL patient.

The elevated NMT activity in PBMC during colonic carcinogenesis may be due to the higher demand of myristoylation of various proteins/oncoproteins which are overexpressed and activated during tumorigenesis. For instance, the levels of the myristoylated tyrosine kinases, $pp^{60c\text{-}src}$ and $pp^{60c\text{-}yes}$ are several folds higher in colonic preneoplastic lesions and neoplasms compared with normal colon cells (Biscardi et al., Adv Cancer Res 1999; 76:61-119). One of the possible outcomes of high NMT activity in neoplasia may be the aberrant myristoylation of proteins which are otherwise not usually myristoylated. For example, N-myristoylation of the normal cellular p21 ras resulted in potent transformation activity. The myristoylation of H-ras and K-ras altered the subcellular localization and significantly affected the activation of MAP kinase.

All references noted above are herein incorporated by reference.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A method for the detection of colorectal cancer comprising the steps of:
    obtaining a blood or bone marrow sample from a patient suspected of having colorectal cancer; and
    detecting the level of N-myristoyltransferase (NMT) or N-myristoyltransferase (NMT) activity in said patient sample and comparing said level to a control value from a blood or bone marrow sample from a subject without colorectal cancer;
    wherein an increased level of NMT or NMT activity in the patient sample relative to the control value is indicative of colorectal cancer in said patient.

2. The method of claim 1 wherein the blood sample comprises peripheral blood mononuclear cells.

3. The method of claim 1 wherein the level of NMT is detected using immunohistochemical analysis.

4. The method of claim 1 wherein the level of NMT is detected by quantifying binding of NMT and an anti-NMT antibody.

5. The method of claim 4 wherein the anti-NMT antibody is a polyclonal antibody.

6. The method of claim 4 wherein the anti-NMT antibody is anti NMT-1.

7. The method of claim 1 wherein NMT activity is detected and compared to the control value.

8. The method of claim 7 wherein NMT activity is detected using a protein myristolation reaction with myristoyl-CoA.

9. The method of claim 1 wherein NMT activity is detected in peripheral blood mononuclear cells.

10. A method for the detection of colorectal cancer comprising the steps of:
    obtaining a blood sample from a patient suspected of having colorectal cancer;
    separating peripheral blood mononuclear cells from the blood sample; and
    comparing the level of N-myristoyltransferase or N-myristoyltransferase activity in said peripheral blood mononuclear cells to a control value from a peripheral blood mononuclear cell sample from a subject without colorectal cancer;
    wherein an increased level of NMT or NMT activity in the patient peripheral blood mononuclear cells relative to the control value is indicative of colorectal cancer in said patient.

11. A method for the detection of colorectal cancer comprising the steps of:
    obtaining a bone marrow sample from a patient suspected of having colorectal cancer;
    separating bone marrow cells from the sample; and
    comparing the level of N-myristoyltransferase or N-myristoyltransferase activity in said bone marrow cells to a control value from a bone marrow cell sample from a subject without colorectal cancer;
    wherein an increased level of NMT or NMT activity in the patient sample relative to the control value is indicative of colorectal cancer in said patient.

12. The method of claim 1, wherein the level of NMT is detected using a kit to quantify binding of NMT and an anti-NMT antibody.

13. The method of claim 12, wherein the anti-NMT antibody is a polyclonal antibody.

14. The method of claim 12, wherein the anti-NMT antibody is anti NMT-1.

* * * * *